(12) United States Patent
Abe et al.

(10) Patent No.: US 10,869,858 B2
(45) Date of Patent: Dec. 22, 2020

(54) THERAPEUTIC AGENT FOR AMYOTROPHIC DISORDERS

(71) Applicant: TOHOKU UNIVERSITY, Miyagi (JP)

(72) Inventors: Takaaki Abe, Miyagi (JP); Masakuni Horiguchi, Osaka (JP); Yuji Matsumoto, Osaka (JP); Maiko Nagayasu, Osaka (JP); Keiichi Murakami, Osaka (JP)

(73) Assignee: Tohoku University, Miyagi (JP)

( * ) Notice: Subject to any disclaimer, the term of this patent is extended or adjusted under 35 U.S.C. 154(b) by 0 days.

(21) Appl. No.: 15/769,793

(22) PCT Filed: Jun. 24, 2016

(86) PCT No.: PCT/JP2016/003044
§ 371 (c)(1),
(2) Date: Jul. 23, 2018

(87) PCT Pub. No.: WO2017/072984
PCT Pub. Date: May 4, 2017

(65) Prior Publication Data
US 2019/0054066 A1 Feb. 21, 2019

(30) Foreign Application Priority Data
Oct. 29, 2015 (JP) .................... 2015-213280

(51) Int. Cl.
*A61K 31/405* (2006.01)
*A61P 21/00* (2006.01)
*A61K 31/192* (2006.01)
*A61K 31/454* (2006.01)

(52) U.S. Cl.
CPC .......... *A61K 31/405* (2013.01); *A61K 31/192* (2013.01); *A61K 31/454* (2013.01); *A61P 21/00* (2018.01)

(58) Field of Classification Search
CPC ...... A61K 31/405; A61K 31/454; A61P 21/00
USPC ........................................................ 514/323
See application file for complete search history.

(56) References Cited

U.S. PATENT DOCUMENTS

2015/0353489 A1  12/2015  Abe et al.

FOREIGN PATENT DOCUMENTS

| CA | 2896437 A1 * | 5/2014 | ........... A61K 31/192 |
| JP | 2015189670 | 11/2015 | |
| WO | WO-2012022467 A2 * | 2/2012 | ............. C07C 50/30 |
| WO | 2014080640 | 5/2014 | |
| WO | WO-2014080640 A1 * | 5/2014 | ........... A61K 31/405 |
| WO | 2014154925 | 10/2014 | |

OTHER PUBLICATIONS

Suzuki et al, Tohuko J. Exp. Med (2015), vol. 236, pp. 225-232. (Year: 2015).*
Koh et al, Eur J Neuroscience, 25 (2007) pp. 1923-1930. (Year: 2007).*
Noh et al, Neuroscience Letters 574 (2014), pp. 53-58. (Year: 2014).*
Kim et al, J Clin Neurol (2014), vol. 10 (4), pp. 342-347. (Year: 2014).*
Suzuki et al, Tohoku J Exp Med (2015), vol. 236, pp. 225-232. (Year: 2015).*

(Continued)

*Primary Examiner* — Craig D Ricci
*Assistant Examiner* — Janet L. Coppins
(74) *Attorney, Agent, or Firm* — Occhiuti & Rohlicek LLP

(57) ABSTRACT

It is an object of the present invention to provide a novel therapeutic agent and method for treating amyotrophic diseases, and more specifically a therapeutic agent and method for treating neurogenic amyotrophic disorders such as amyotrophic lateral sclerosis (ALS) and myogenic amyotrophic disorders such as sarcopenia or disuse muscle atrophy. Provided is a therapeutic agent for amyotrophic diseases that comprises one or more compounds selected from the group consisting of compounds represented by the formula (I), the formula (II) and the formula (III), and pharmaceutically acceptable salts of the compounds when $R^3$ represents OH.

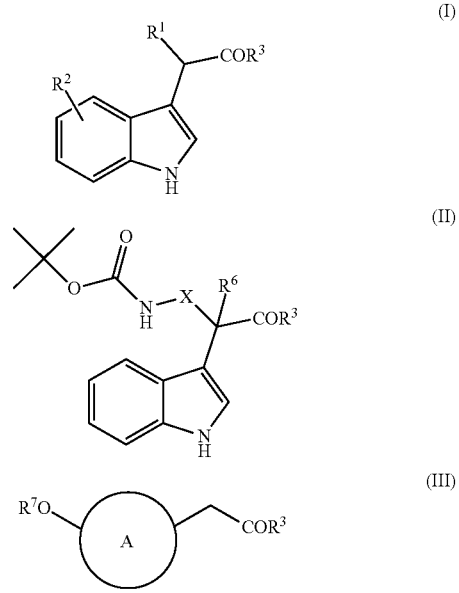

1 Claim, 2 Drawing Sheets

(56) References Cited

OTHER PUBLICATIONS

Notification of Transmittal of Translation of the International Preliminary Report on Patentability and the English Translation of the International Report on Patentability issued by The International Bureau of WIPO for International Application No. PCT/JP2016/003044 dated May 11, 2018, 9 pages.

Sato et al., "ALS Model Mouse ni Okeru Teisanso Stress Sensor no Kino Ijo," the 55th Annual Meeting of the Japanese Society of Neurology Program Shorokushu, 2014, 576, entire text. English translation also provided.

Zhang Ziyan, Jingqi Yan, Yanzhong Chang, S. ShiDu Yan, and Honglian Shi. "Hypoxia inducible factor-1 as a target for neurodegenerative diseases." Current medicinal chemistry 18, No. 28 (2011): 4335-4343.

Petri, Susanne, Noel Y. Calingasan, Osama A. Alsaied, Elizabeth Wille, Mahmoud Kiaei, Jonathan E. Friedman, Oxana Baranova, Juan C. Chavez, and M. Flint Beal. "The lipophilic metal chelators DP-109 and DP-460 are neuroprotective in a transgenic mouse model of amyotrophic lateral sclerosis." Journal of neurochemistry 102, No. 3 (2007): 991-1000.

Suzuki, Takehiro, Hiroaki Yamaguchi, Motoi Kikusato, Tetsuro Matsuhashi, Akihiro Matsuo, Takeya Sato, Yuki Oba et al. "Mitochonic acid 5 (MA-5), a derivative of the plant hormone indole-3-acetic acid, improves survival of fibroblasts from patients with mitochondrial diseases." Retrieved from http://www.sasappa.co.jp/online/abstract/tmp/1/236/html/0102360309.html on Aug. 15, 2016.

Suzuki, Takehiro, Hiroaki Yamaguchi, Motoi Kikusato, Tetsuro Matsuhashi, Akihiro Matsuo, Takeya Sato, Yuki Oba et al. "Mitochonic acid 5 (MA-5), a derivative of the plant hormone indole-3-acetic acid, improves survival of fibroblasts from patients with mitochondrial diseases." The Tohoku journal of experimental medicine 236, No. 3 (2015): 225-232. Retrieved from http://www.journal.med.tohoku.ac.jp/2363/236_225.pdf, Jun. 26, 2015.

Suzuki, Takehiro, Hiroaki Yamaguchi, Motoi Kikusato, Tetsuro Matsuhashi, Akihiro Matsuo, Takeya Sato, Yuki Oba et al. "Mitochonic acid 5 (MA-5), a derivative of the plant hormone indole-3-acetic acid, improves survival of fibroblasts from patients with mitochondrial diseases." The Tohoku journal of experimental medicine 236, No. 3 (2015): 225-232.

\* cited by examiner

[Figure 1]
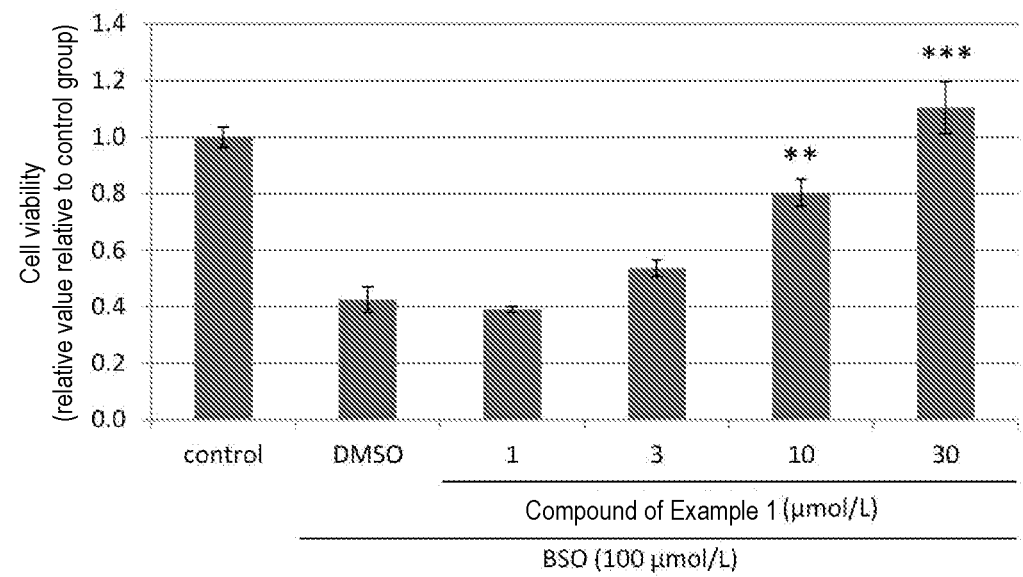
[Figure 2]
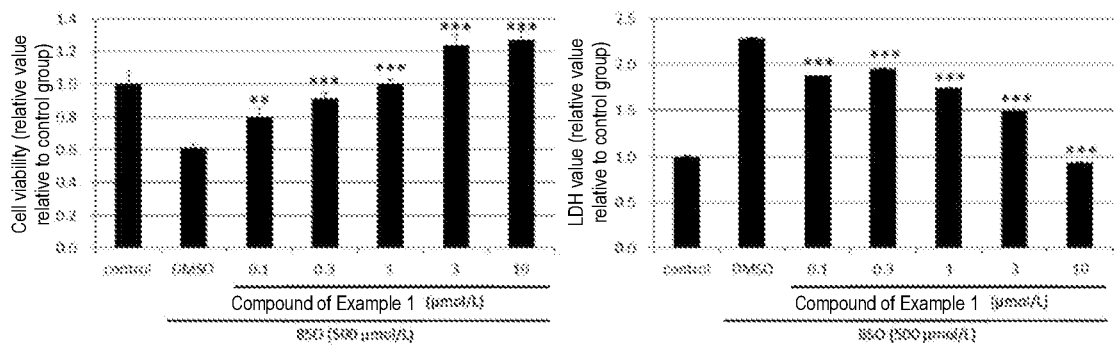

[Figure 3]
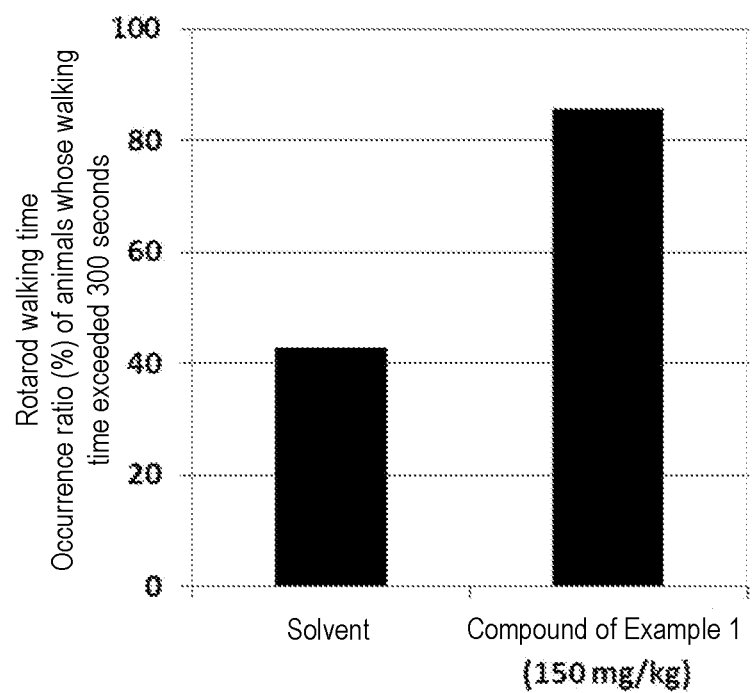

THERAPEUTIC AGENT FOR AMYOTROPHIC DISORDERS

CROSS REFERENCE TO RELATED APPLICATIONS

This application is a National Phase under 35 USC 371 of International Application No. PCT/JP2016/003044 filed on Jun. 24, 2016, which claims priority to Japanese Application No. 2015-213280 filed Oct. 29, 2015, the contents of which are hereby incorporated by reference in their entirety.

TECHNICAL FIELD

The present invention relates to a therapeutic agent and pharmaceutical composition for inhibiting muscle atrophy. More specifically, it relates to a therapeutic agent and pharmaceutical composition for neurogenic amyotrophic disorders such as amyotrophic lateral sclerosis (ALS) and myogenic amyotrophic disorders such as sarcopenia or disuse muscle atrophy.

BACKGROUND ART

The skeletal muscle is a tissue involved in the movement and postural maintenance of each part of the body, and innervated by motor nerves consisting of upper motor neurons that project on anterior horn cells in the spinal cord from the brain and the lower motor neurons that project on the muscle tissue from anterior horn cells in the spinal cord. The muscle tissue of the skeletal muscle is composed of multiple bundles of muscle fibers containing myofibrils.

The muscle atrophy refers to atrophy of muscle fibers due to decrease in myofibrils, and causes morbid muscle weakness. Diseases involving muscle atrophy can be broadly divided on the basis of their etiologies into two types: amyotrophic diseases based on disorders of the motor nerves (neurogenic amyotrophic diseases) and amyotrophic diseases based on disorders of muscle tissues themselves (myogenic amyotrophic disorders).

Representative examples of the neurogenic amyotrophic diseases include amyotrophic lateral sclerosis (ALS), spinal muscular atrophy, spinobulbar muscular atrophy and Guillain-Barre syndrome. Among them, ALS is a disease with a relatively high morbidity among neurogenic amyotrophic diseases, but the cause of its onset is still unknown. It is a disease with poor prognosis that causes remarkable muscle atrophy in the whole body as a symptom, resulting in movement disorders, dysarthria, aphagia, respiratory failure or the like. The effect of riluzole, an ALS therapeutic drug currently used in Japan only delays ALS symptom progression by several months, and there is no effective method for treating ALS. There is also currently no effective method for treating other neurogenic amyotrophic diseases. Therefore, there is a need for an effective therapeutic agent for these neurogenic amyotrophic diseases.

Examples of the myogenic amyotrophic diseases include an inherited muscular disease such as muscular dystrophy, congenital myopathy or distal myopathy as well as a non-inherited muscular disease such as age-related muscle atrophy (sarcopenia) or disuse muscle atrophy caused by decreased activities due to an illness, a bedridden state or the like. Particularly, since sarcopenia and disuse muscular atrophy are expected to increase with rapid advancement of the aging society, effective methods for treating these amyotrophic diseases are required, but there is currently no fundamental therapy. Therefore, there is a need for an effective therapeutic agent for the myogenic amyotrophic diseases.

Patent Document 1 discloses an indole acetic acid derivative having an erythropoietin production promoting effect and the like.

PRIOR ART DOCUMENTS

Patent Documents

Patent Document 1: WO 2014/080640

SUMMARY OF THE INVENTION

Object to be Solved by the Invention

It is an object of the present invention to provide a novel therapeutic agent and method for treating amyotrophic diseases. More specifically, it is an object of the present invention to provide a therapeutic agent and method for treating neurogenic amyotrophic disorders such as amyotrophic lateral sclerosis (ALS) and myogenic amyotrophic disorders such as sarcopenia or disuse muscle atrophy.

Means to Solve the Object

The present inventors have conducted diligent research and, as a result, have found that compounds represented by the following formulae and pharmaceutically acceptable salts thereof (hereinafter sometimes abbreviated as "compounds of the present invention" as necessary) have an excellent amelioration effect on various amyotrophic diseases, and have thus completed the present invention.

More specifically, the present invention is as follows:

[1] A therapeutic agent for amyotrophic diseases, comprising one or more compounds selected from the group consisting of compounds represented by the formula (I):

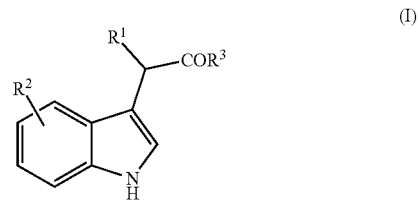

wherein $R^1$ represents a benzoylmethyl group having a benzene ring unsubstituted or substituted with an alkyl group having 1 to 7 carbon atoms, an alkoxyl group having 1 to 7 carbon atoms, a fluorine atom and/or a chlorine atom; a linear or branched alkyl group having 4 to 6 carbon atoms unsubstituted or substituted with a fluorine atom; or methylene or ethylene substituted with a phenyl group or a cyclopentyl group, wherein the phenyl group is optionally further substituted with one or more phenyl groups;

$R^2$ is selected from the group consisting of hydrogen, an alkyl group having 1 to 4 carbon atoms, an alkoxyl group having 1 to 7 carbon atoms, a fluorine atom and a chlorine atom with which an indole is substituted at 4, 5, 6 and/or 7 positions/position;

$R^3$ represents a group selected from any one of OH, $OR^4$, $NHR^4$ and $NR^4R^5$; and R⁴ and R⁵, which are the same or different, each represent a substituted or unsubstituted alkyl group having 1 to 4 carbon atoms, the formula (II):

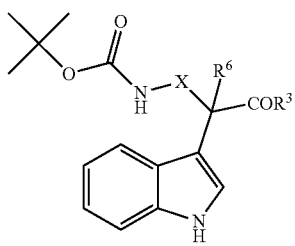

(II)

wherein
R⁶ represents hydrogen or a methyl group;
X represents an alkylene group having 4 to 6 carbon atoms or an ether group having 4 carbon atoms;
R³ represents a group selected from any one of OH, OR⁴, NHR⁴ and NR⁴R⁵; and
R⁴ and R⁵, which are the same or different, each represent a substituted or unsubstituted alkyl group having 1 to 4 carbon atoms, and the formula (III):

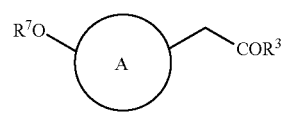

(III)

wherein A represents indole or naphthalene, provided that when A represents indole, indole is substituted with an acetate group and R⁷O at positions 3 and 5, respectively, and when A represents naphthalene, naphthalene is substituted with an acetate group and R⁷O at positions 1 and 7, respectively, wherein R⁷ represents an alkyl group having 1 to 5 carbon atoms or a benzyl group, whose benzene ring is optionally substituted with one or more alkyl groups having 1 to 3 carbon atoms or one or more alkoxy groups having 1 to 3 carbon atoms; R³ represents a group selected from any one of OH, OR⁴, NHR⁴ and NR⁴R⁵; and R⁴ and R⁵, which are the same or different, each represent a substituted or unsubstituted alkyl group having 1 to 4 carbon atoms,
and pharmaceutically acceptable salts of the compounds when R³ represents OH (hereinafter also sometimes collectively referred to as "compound group of the present invention").

[2] The therapeutic agent according to [1], wherein the compound is a compound represented by the formula (I).

[3] The therapeutic agent according to [2], wherein R¹ represents a benzoylmethyl group having a benzene ring substituted with a group or 1 to 5 groups being the same or different, selected from the group consisting of an alkyl group having 1 to 4 carbon atoms, an alkoxyl group having 1 to 4 carbon atoms, a fluorine atom and a chlorine atom.

[4] The therapeutic agent according to [2] or [3], wherein R² represents hydrogen.

[5] The therapeutic agent according to any one of [1] to [4], wherein R³ represents OH.

[6] The therapeutic agent according to [1], wherein the compound is selected from the following compounds:

4-(2,4-difluorophenyl)-2-(1H-indol-3-yl)-4-oxobutanoic acid (Example 1),
4-(4-fluorophenyl)-2-(1H-indol-3-yl)-4-oxobutanoic acid (Example 2), and
4-(4-chlorophenyl)-2-(1H-indol-3-yl)-4-oxobutanoic acid (Example 3).

[7] The therapeutic agent according to any one of [1] to [6], wherein the amyotrophic disease is a neurogenic amyotrophic disease or a myogenic amyotrophic disease.

[8] The therapeutic agent according to [7], wherein the neurogenic amyotrophic disease is amyotrophic lateral sclerosis (ALS), spinal muscular atrophy, spinobulbar muscular atrophy, Guillain-Barre syndrome, multiple sclerosis, chronic inflammatory demyelinating polyneuropathy, myasthenia gravis or Charcot-Marie-Tooth disease.

[9] The therapeutic agent according to [7], wherein the myogenic amyotrophic disease is progressive muscular dystrophy, myotonic dystrophy, congenital myopathy, metabolic myopathy, distal myopathy, inflammatory myopathy, age-related muscle atrophy (sarcopenia), Barth syndrome or disuse muscle atrophy.

Other embodiments of the present invention include a method for treating amyotrophic diseases comprising administrating one or more compounds selected from the compound group of the present invention to a patient in need thereof; one or more compounds selected from the compound group of the present invention for use as a therapeutic agent for amyotrophic diseases; one or more compounds selected from the compound group of the present invention for use in treatment of amyotrophic diseases; and use of one or more compounds selected from the compound group of the present invention in producing a therapeutic agent for amyotrophic diseases.

Effect of the Invention

The compounds of the present invention have an excellent amelioration effect on various amyotrophic diseases. Specifically, it can inhibit muscle weakness and progression of muscle atrophy in amyotrophic diseases and thereby ameliorate symptoms induced by amyotrophic diseases, such as movement disorders, dysarthria, aphagia and respiratory failure.

BRIEF DESCRIPTION OF DRAWINGS

FIG. 1 is a graph showing the results of analysis of cell viability by culturing ALS patient-derived fibroblasts treated with a glutathione synthesis inhibitor, L-buthionine(S, R)sulfoximine (BSO) in the presence of the compound of Example 1. The vertical axis shows the relative ratio when the cell viability of the ALS patient-derived fibroblasts cultured in the absence of both BSO and the compound (control group in the figure) is 1, and each value represents the mean value±standard error of three cases per group. In the Dunnett type multiple comparison test with the BSO and DMSO addition group (DMSO group in the figure) as a control,  in the figure indicates P value is less than 0.01 and * in the figure indicates P value is less than 0.001.

FIG. 2 is a graph showing the results of analysis of the cell viability (left) and the degree of cell damage (right) by culturing ALS patient-derived fibroblasts treated with BSO in the presence of the compound of Example 1. The vertical axes show the relative ratio when the cell viability and the degree of cell damage of the ALS patient-derived fibroblasts cultured in the absence of both BSO and the compound (control groups in the figures) are 1, respectively and each value represents the mean value±standard error of five cases per group. In the Dunnett type multiple comparison test with the BSO and DMSO addition group (DMSO group in the figure) as a control,  in the figure indicates P value is less than 0.01 and * in the figure indicates P value is less than 0.001.

FIG. 3 is a graph showing the results of the rotarod test performed 16 days after administration start date, after orally administering to wobbler mice the compound of Example 1 (150 mg/kg) or a solvent, a 0.5% aqueous solution of methyl cellulose once a day. The vertical axis represents the occurrence ratio (%) of animals whose rotarod walking time exceeded 300 seconds in each group.

MODE OF CARRYING OUT THE INVENTION

The compounds of the present invention have preventive and therapeutic effects on amyotrophic diseases. Such amyotrophic diseases are not particularly limited as long as they are diseases accompanied by muscle atrophy, and specifically includes a neurogenic amyotrophic disease such as amyotrophic lateral sclerosis (ALS), spinal muscular atrophy, spinobulbar muscular atrophy, Guillain-Barre syndrome, multiple sclerosis, chronic inflammatory demyelinating polyneuropathy, myasthenia gravis and Charcot-Marie-Tooth disease; and myogenic amyotrophic diseases such as progressive muscular dystrophy, myotonic dystrophy, congenital myopathy, metabolic myopathy, distant myopathy, inflammatory myopathy, age-related muscle atrophy (sarcopenia), Barth syndrome and disuse muscle atrophy.

In the present invention, the term "prevention/preventive" refers to an act of administering an active ingredient of the present invention to a healthy individual who has not developed a disease, for example, for the purpose of preventing the onset of a disease. The term "treatment/treating" refers to an act of administering an active ingredient of the present invention to an individual (patient) diagnosed as developing a disease by a doctor.

The therapeutic agent for amyotrophic diseases of the present invention may be formulated, as necessary, with one or more ingredients such as conventional pharmaceutically acceptable carriers, binders, stabilizers, excipients, diluents, pH buffers, disintegrants, isotonic agents, additives, coating agents, solubilizing agents, lubricating agents, glidants, dissolution aids, lubricants, flavoring agents, sweetening agents, solvents, gelling agents or nutrients, for example. Specific examples of such ingredients include water, a physiological saline, animal fat and oil, vegetable oil, lactose, starch, gelatin, crystalline cellulose, gum, talc, magnesium stearate, hydroxypropyl cellulose, polyalkylene glycol, polyvinyl alcohol and glycerin.

Examples of modes of administration include an oral administration in such a dosage form as a powder, a granule, a tablet, a capsule, a syrup or a suspension; and a parenteral administration such as an injection in such a dosage form as a solution, an emulsion or a suspension, an intranasal administration in such a dosage form as a spray or a transdermal administration in such a dosage form as a cataplasm or a tape.

The dosage of the therapeutic agent for amyotrophic diseases of the present invention is appropriately determined depending on the age, body weight, sex, symptoms, susceptibility to a drug and the like of a subject. The therapeutic agent of the present invention is usually administered in a dosage ranging of about 0.01 to 5,000 mg/kg body weight/day, preferably about 0.1 to 3,000 mg/kg body weight/day and more preferably about 1 to 300 mg/kg body weight/day in one or more divided doses daily (for example, 2 to 4 times a day), but may be adjusted depending on the degree of amelioration.

The therapeutic agent for amyotrophic diseases of the present invention is not particularly limited as long as it contains one or more compounds as active ingredients selected from the compound group of the present invention. The compounds included in the compound group of the present invention will be illustrated in detail as follows.

In one aspect of the present invention, $R^1$ in the above general formula (I) represents a benzoylmethyl group having a benzene ring unsubstituted or substituted with an alkyl group having 1 to 7 carbon atoms, an alkoxyl group having 1 to 7 carbon atoms, a fluorine atom and/or chlorine atom. The benzene ring in such a benzoylmethyl group is optionally substituted. Examples of the substituted benzoylmethyl group include a benzoylmethyl group having, on a benzene ring, 1 to 5 alkyl groups having 1 to 7 carbon atoms, a 1 to 5 alkoxyl groups having 1 to 7 carbon atoms, 1 to 5 fluorine atoms or 1 to 5 chlorine atoms, or 1 to 5 groups, which are the same or different, selected from the group consisting of an alkyl group having 1 to 4 carbon atoms, an alkoxyl group having 1 to 4 carbon atoms, a fluorine atom or a chlorine atom.

Examples of the alkyl group having 1 to 7 carbon atoms include a methyl group, an ethyl group, a propyl group, an isopropyl group, a n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, a n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4,4-dimethylpentyl group and a 1-propylbutyl group.

Examples of the alkoxyl group having 1 to 7 carbon atoms include a methoxy group, an ethoxy group, a propoxy group, an isopropoxy group, a n-butoxy group, an isobutoxy group, a sec-butoxy group, a tert-butoxy group, a n-pentoxy group, a 1-methylbutoxy group, a 2-methylbutoxy group, a 3-methylbutoxy group, a 1-ethylpropoxy group, a 1,1-dimethylpropoxy group, a 1,2-dimethylpropoxy group, a 2,2-dimethylpropoxy group, a n-hexyloxy group, a 1-methylpentyloxy group, a 2-methylpentyloxy group, a 3-methylpentyloxy group, a 4-methylpentyloxy group, a 1,1-dimethylbutoxy group, a 1,2-dimethylbutoxy group, a 1,3-dimethylbutoxy group, a 2,2-dimethylbutoxy group, a 2,3-dimethylbutoxy group, a 3,3-dimethylbutoxy group, a 1,1,2-trimethylpropoxy group, a 1-ethylbutoxy group, a 2-ethylbutoxy group, a 1-ethyl-1-methylpropoxy group, a 1-ethyl-2-methylpropoxy group, a n-heptyloxy group, a 1-methylhexyloxy group, a 2-methylhexyloxy group, a 3-methylhexyloxy group, a 4-methylhexyloxy group, a 5-methylhexyloxy group, a 1-ethylpentyloxy group, a 2-ethylpentyloxy group, a 3-ethylpentyloxy group, a 4,4-dimthylpentyloxy group and a 1-propylbutoxy group.

In another aspect of the present invention, $R^1$ in the above general formula (I) represents a linear or branched alkyl group having 4 to 6 carbon atoms unsubstituted or substituted with one or more fluorine atoms. Examples of the linear or branched alkyl group having 4 to 6 carbon atoms unsubstituted or substituted with one or more fluorine atoms include a n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group and these groups which are fluorinated; preferably a 1-ethylbutyl group, a 2-ethylbutyl group, a 1-methylpentyl group, a 2-methylpentyl group, a 3-methylpentyl group, a 4-methylpentyl group, a 5-methylpentyl group, a 3,3,4,4,4-pentafluorobutyl group, a 4,4,5,5,5-pentafluoropentyl group and a 5,5,6,6,6-pentafluorohexyl group; more preferably a 2-ethylbutyl group, a 2-methylpentyl group, a 3-methylpentyl group and a 4,4,5,5,5-pentafluoropentyl group; and most preferably a 4,4,5,5,5-pentafluoropentyl group.

In further another aspect of the present invention, $R^1$ in the above general formula (I) represents methylene or ethylene substituted with a phenyl group or a cyclopentyl group, wherein the phenyl group is optionally further substituted with one or more phenyl groups. Examples of the methylene or ethylene substituted with a phenyl group or a cyclopentyl group include a benzyl group, a 2-phenethyl group, a cyclopentylmethyl group or a 2-cyclopentylethyl group. Examples of the benzyl group or 2-phenethyl group substituted with one or more phenyl groups include a 3-phenylbenzyl group, a 4-phenylbenzyl group, a 3,5-diphenylbenzyl group, a 2-(1,1'-biphenyl-3-yl)-ethyl group, a 2-(1,1'-biphenyl-4-yl)-ethyl group and a 2-(3,5-diphenylphenyl)-ethyl group. Suitable examples of $R^1$ in the above general formula (I) include a 2-phenethyl group, a cyclopentylmethyl group, a 2-cyclopentylethyl group and a 2-(1,1'-biphenyl-3-yl)-ethyl group.

$R^2$ in the above general formula (I) represents a group with which an indole skeleton is substituted at position 4, 5, 6 and 7 thereof, and the indole skeleton may be substituted by one or more substituents at each position. Examples of $R^2$ include hydrogen, an alkyl group having 1 to 4 carbon atoms, an alkoxyl group having 1 to 7 carbon atoms, a fluorine atom and a chlorine atom. Examples of the alkyl group having 1 to 4 carbon atoms include a methyl group, an ethyl group, propyl group, an isopropyl group, a n-butyl group, an isobutyl group, a sec-butyl group and a tert-butyl group. Examples of the alkoxyl group having 1 to 7 carbon atoms include a methoxy group, an ethoxy group, a propoxy group, an isopropoxy group, a n-butoxy group, a isobutoxy group, a sec-butoxy group, a tert-butoxy group, a n-pentoxy group, a 1-methylbutoxy group, a 2-methylbutoxy group, a 3-methylbutoxy group, a 1-ethylpropoxy group, a 1,1-dimethylpropoxy group, a 1,2-dimethylpropoxy group, a 2,2-dimethylpropoxy group, a n-hexyloxy group, a 1-methylpentyloxy group, a 2-methylpentyloxy group, a 3-methylpentyloxy group, a 4-methylpentyloxy group, a 1,1-dimethylbutoxy group, a 1,2-dimethylbutoxy group, a 1,3-dimethylbutoxy group, a 2,2-dimethylbutoxy group, a 2,3-dimethylbutoxy group, a 3,3-dimethylbutoxy group, a 1,1,2-trimethylpropoxy group, a 1-ethylbutoxy group, a 2-ethylbutoxy group, a 1-ethyl-1-methylpropoxy group, a 1-ethyl-2-methylpropoxy group, a n-heptyloxy group, a 1-methylhexyloxy group, a 2-methylhexyloxy group, a 3-methylhexyloxy group, a 4-methylhexyloxy group, a 5-methylhexyloxy group, a 1-ethylpentyloxy group, a 2-ethylpentyloxy group, a 3-ethylpentyloxy group, a 4,4-dimethylpentyloxy group and a 1-propylbutoxy, and preferably hydrogen, an ethoxy group, fluorine atom or a chlorine atom.

$R^4$ and $R^5$ in the above general formula (I), which are the same or different, each represent a substituted or unsubstituted alkyl group having 1 to 4 carbon atoms. Examples of the substituted or unsubstituted alkyl group having 1 to 4 carbon atoms include a methyl group, an ethyl group, a propyl group, an isopropyl group, a n-butyl group, an isobutyl group, a sec-butyl group and a tert-butyl group, pyrrolidine which $R^4$ and $R^5$ form together with nitrogen, and these substituted with a methoxy group, a phenyl group, a fluorine atom and a chlorine atom; preferably a methyl group, a monochloromethyl group, an ethyl group, a 2-methoxyethyl group, a 2,2,2-trichloroethyl group, a 1-phenylethyl group, a 2-phenylethyl group, a methoxyethyl group, an isopropyl group, a hexafluoroisopropyl group and pyrrolidine; and more preferably a methyl group and an ethyl group.

The compound represented by the general formula (I) wherein $R^1$ represents 4-chlorobenzoylmethyl group, $R^2$ represents hydrogen and $R^3$ represents OH represents Compound #2 in Table 1 below; the compound represented by the general formula (I) wherein $R^1$ represents 4-fluorobenzoylmethyl group, $R^2$ represents hydrogen and $R^3$ represents OH represents Compound #4 in Table 1 below; the compound represented by the general formula (I) wherein $R^1$ represents 2,4-difluorobenzoylmethyl group, $R^2$ represents hydrogen and $R^3$ represents OH represents Compound #5 in Table 1 below; the compound represented by the general formula (I) wherein $R^1$ represents 4,4,5,5,5-pentafluoropentyl group, $R^2$ represents hydrogen and $R^3$ represents OH represents Compound #21 in Table 1 below; and the compound represented by the general formula (I) wherein $R^1$ represents 2-cyclopentylethyl group, $R^2$ represents hydrogen and $R^3$ represents OH represents Compound #24 in Table 1 below. In addition to these compounds, specific examples of the compound represented by the general formula (I) include Compounds #2, 4, 5 and 20 in Table 1 below, Compounds #17 to 19 in Table 1 below, Compounds #22 and 23 in Table 1 below, and Compound #25 in Table 1 below.

X in the above general formula (II) represents a linear alkylene group having 4 to 6 carbon atoms, that is, butylene-$(CH_2)_4$—, pentylene-$(CH_2)_5$— and hexylene-$(CH_2)_6$—, or an ether group having 4 carbon atoms. Examples of the ether group having 4 carbon atoms include a methylene-O-propylene group, an ethylene-O-ethylene group and a propylene-O-methylene group, and preferably butylene, hexylene and an ethylene-O-ethyl group.

$R^4$ and $R^5$ in the above general formula (II), which are the same or different, each represent a substituted or unsubstituted alkyl group having 1 to 4 carbon atoms. Examples of the substituted or unsubstituted alkyl group having 1 to 4 carbon atoms include a methyl group, an ethyl group, a propyl group, an isopropyl group, a n-butyl group, an isobutyl group, a sec-butyl group and a tert-butyl group, pyrrolidine which $R^4$ and $R^5$ form together with nitrogen, and these substituted with a methoxy group, a phenyl group, a fluorine atom and a chlorine atom; preferably a methyl group, a monochloromethyl group, an ethyl group, a 2,2,2-trichloromethyl group, a 1-phenylethyl group, a 2-phenylethyl group, a methoxyethyl group, an isopropyl group, a hexafluoroisopropyl group and pyrrolidine; and more preferably a methyl group and an ethyl group.

The compound represented by the general formula (II) wherein X represents butylene, $R^6$ represents hydrogen and $R^3$ represents OH represents Compound #15 in Table 1 below. In addition to Compound #15, specific examples of the compound represented by the general formula (II) include Compound #13 in Table 1 below and Compound #14 in Table 1 below.

$R^7$ in the above general formula (III) represents an alkyl group having 1 to 5 carbon atoms or a benzyl group. Examples of the linear or branched alkyl group having 1 to 5 carbon atoms include a methyl group, an ethyl group, a propyl group, an isopropyl group, a n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group and a 2,2-dimethylpropyl group. The benzene ring of the above benzyl group is optionally substituted with one or more alkyl groups having 1 to 3 carbon atoms or one or more alkoxy groups having 1 to 3 carbon atoms. Examples of the alkyl group having 1 to 3 carbon atoms include a methyl group, an ethyl group, a n-propyl group and an isopropyl group; and examples of the alkoxy group having 1 to 3 carbon atoms include a methoxy group, an ethoxy groups, a n-propoxy group and an isopropoxy group. $R^7$ in the above general formula (III) preferably represents a methyl group, an ethyl group, a propyl group, n-butyl group, a n-pentyl and a 3,5-dimethoxybenzyl group, and more preferably a 3,5-dimethoxybenzyl group.

$R^4$ and $R^5$ in the above general formula (III), which are the same or different, each represent a substituted or unsubstituted alkyl group having 1 to 4 carbon atoms. Examples of the substituted or unsubstituted alkyl group having 1 to 4 carbon atoms include a methyl group, an ethyl group, a propyl group, an isopropyl group, a n-butyl group, an isobutyl group, a sec-butyl group and a tert-butyl group, pyrrolidine which $R^4$ and $R^5$ form together with nitrogen, and these substituted with a methoxy group, a phenyl group, a fluorine atom and a chlorine atom; preferably a methyl group, a monochloromethyl group, an ethyl group, a 2,2,2-trichloromethyl group, a 1-phenylethyl group, a 2-phenylethyl group, a methoxyethyl group, an isopropyl group, a hexafluoroisopropyl group and pyrrolidine; and more preferably a methyl group and an ethyl group.

The compound represented by the general formula (III) wherein A represents indole, $R^7$ represents a 3,5-dimethoxybenzyl group and $R^3$ represents OH represents Compound #35 in Table 1 below. In addition to Compound #35, specific examples of the compound represented by the general formula (II) include Compounds #36 to #38 in Table 1 below and Compounds #33 and #34 in Table 1 below.

When the compound selected from the compound group of the present invention has an asymmetric carbon atom and a chiral point involved in an axial chirality, such a compound includes all possible optical isomers, which can be used in any ratio. For example, a certain optically active compound can be used as an enantiomer and a racemic form and a mixture of enantiomers in any ratio. When plural chiral points are present, a mixture of diastereomers in any ratio may be used.

Examples of the pharmaceutically acceptable salts in the compound group of the present invention include a metal salt formed with aluminum, calcium, lithium, magnesium, potassium, sodium or zinc, and an organic salt formed with N,N'-dibenzylethylenediamine, chloroprocaine, choline, diethanolamine, ethylenediamine, N-methylglucamine, lysine and procaine.

The compounds of the present invention can be produced, for example, by the method described in the above Patent Document 1. Specifically, for example, the following compounds can be produced.

TABLE 1

Exemplary compounds which can be produced

| Compound Number | Compound Name | Structure |
|---|---|---|
| #1 | 4-Phenyl-2-(4-chloro-1H-indol-3-yl)-4-oxobutanoic acid | 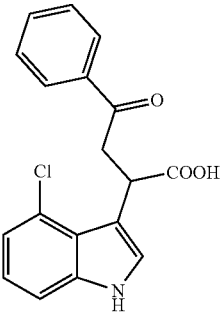 [SMILES: O=C(CC(C(=O)O)c1c[nH]c2cccc(Cl)c12)c1ccccc1] |

TABLE 1-continued
Exemplary compounds which can be produced
| Compound Number | Compound Name | Structure |
|---|---|---|
| #2 | 4-(4-Chlorophenyl)-2-(1H-indol-3-yl)-4-oxobutanoic acid | 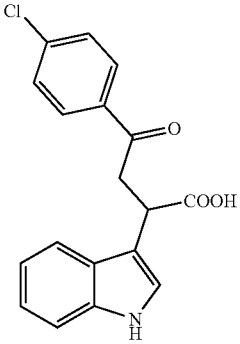 [SMILES: O=C(CC(C(=O)O)c1c[nH]c2ccccc12)c1ccc(Cl)cc1] |
| #4 | 4-(4-Fluorophenyl)-2-(1H-indol-3-yl)-4-oxobutanoic acid | 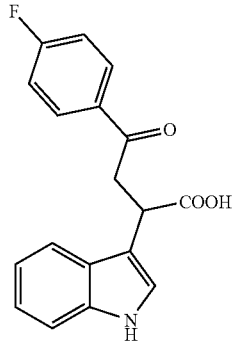 [SMILES: O=C(CC(C(=O)O)c1c[nH]c2ccccc12)c1ccc(F)cc1] |
| #5 | 4-(2,4-Difluorophenyl)-2-(1H-indol-3-yl)-4-oxobutanoic acid | 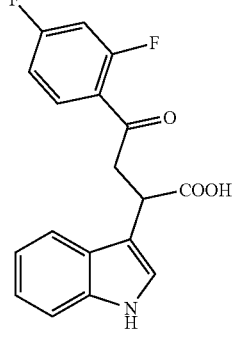 |
| #6 | 4-(2,4-Dimethylphenyl)-2-(1-propyl-1H-indol-3-yl)-4-oxobutanoic acid | 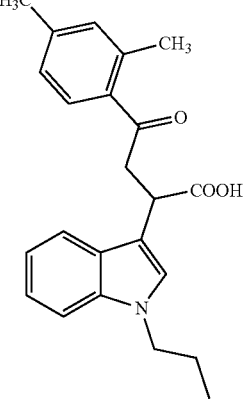 |

TABLE 1-continued

Exemplary compounds which can be produced

| Compound Number | Compound Name | Structure |
|---|---|---|
| #7 | 4-Phenyl-2-(1H-5-ethoxyindol-3-yl)-4-oxobutanoic acid | 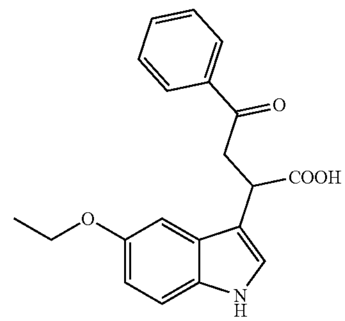 [SMILES: CCOc1ccc2[nH]cc(C(CC(=O)c3ccccc3)C(=O)O)c2c1] |
| #8 | α-2-(1-Acetyl-4-piperidinyl)-ethyl-3-indoleacetic acid | 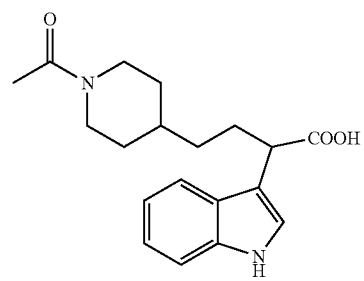 [SMILES: CC(=O)N1CCC(CCC(C(=O)O)c2c[nH]c3ccccc23)CC1] |
| #9 | α-2-(1-Acetyl-4-piperidinyl)-methyl-3-indoleacetic acid | 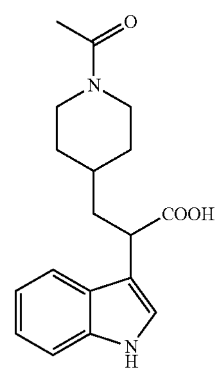 [SMILES: CC(=O)N1CCC(CC(C(=O)O)c2c[nH]c3ccccc23)CC1] |
| #10 | α-[N-(1-acetylpyrrolidine-2-carbonyl)-4-aminobutyl]-3-indoleacetic acid | 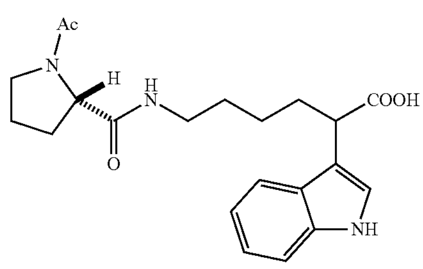 [SMILES: CC(=O)N1CCC[C@H]1C(=O)NCCCCC(C(=O)O)c1c[nH]c2ccccc12] |
| #11 | α-[N-(1-acetylpyrrolidine-2-carbonyl)-2-(2-aminoethoxy]-1-ethyl]-3-indoleacetic acid | 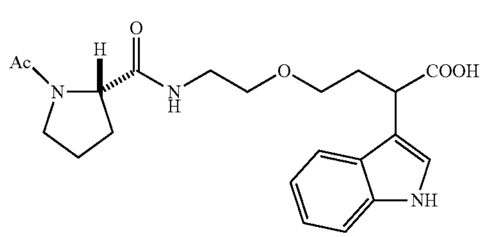 |

TABLE 1-continued

Exemplary compounds which can be produced

| Compound Number | Compound Name | Structure |
|---|---|---|
| #12 | α-[N-tert-butoxycarbonyl-6-amino-1-hexyl)-α-(1-naphthyl)-acetic acid | 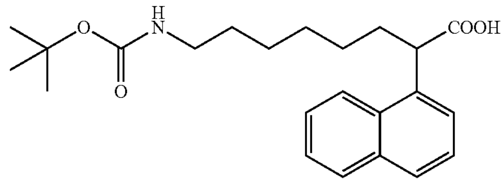 [SMILES: CC(C)(C)OC(=O)NCCCCCCC(C(=O)O)c1cccc2ccccc12] |
| #13 | α-(N-tert-butoxycarbonyl-6-amino-1-hexyl)-α-methyl-3-indoleacetic acid | 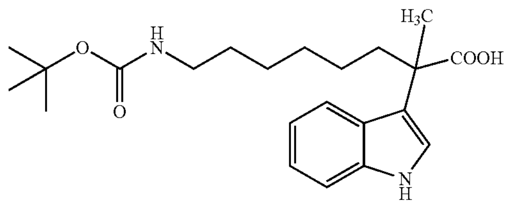 [SMILES: CC(C)(C)OC(=O)NCCCCCCC(C)(C(=O)O)c1c[nH]c2ccccc12] |
| #14 | α-[2-(N-tert-butoxycarbonyl-2-aminoethoxy)-1-ethyl]-3-indoleacetic acid | 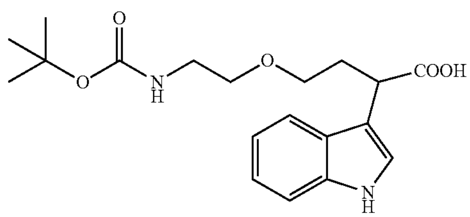 [SMILES: CC(C)(C)OC(=O)NCCOCCC(C(=O)O)c1c[nH]c2ccccc12] |
| #15 | α-(N-tert-butoxycarbonyl-4-amino-1-butyl)-3-indoleacetic acid | 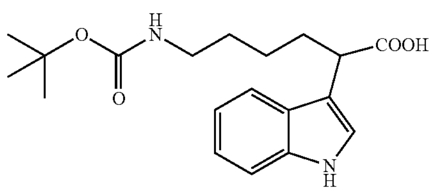 [SMILES: CC(C)(C)OC(=O)NCCCCC(C(=O)O)c1c[nH]c2ccccc12] |
| #17 | α-(2-Ethyl-1-butyl)-3-indoleacetic acid | 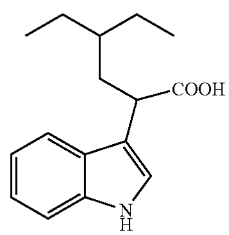 [SMILES: CCC(CC)CC(C(=O)O)c1c[nH]c2ccccc12] |
| #18 | α-(3-Methyl-1-pentyl)-3-indoleacetic acid | 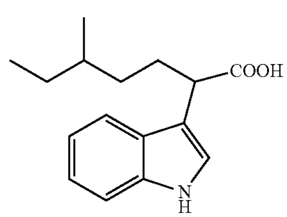 [SMILES: CCC(C)CCC(C(=O)O)c1c[nH]c2ccccc12] |
| #19 | α-(2-Methyl-1-pentyl)-3-indoleacetic acid | 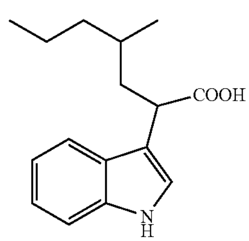 [SMILES: CCCC(C)CC(C(=O)O)c1c[nH]c2ccccc12] |

TABLE 1-continued

Exemplary compounds which can be produced

| Compound Number | Compound Name | Structure |
|---|---|---|
| #20 | 4-Phenyl-2-(1H-indol-3-yl)-4-oxobutanoic acid | 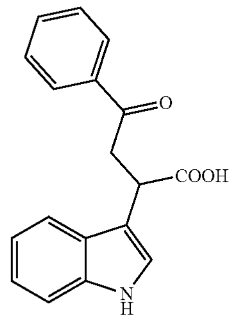 [SMILES: O=C(CC(C(=O)O)c1c[nH]c2ccccc12)c1ccccc1] |
| #21 | α-(4,4,5,5,5-Pentafluoro-1-pentyl)-3-indoleacetic acid | 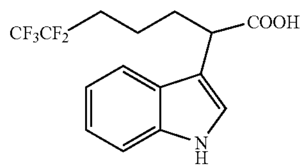 |
| #22 | α-[2-(1,1'-Biphenyl-3-yl)-1-ethyl]-3-indoleacetic acid | 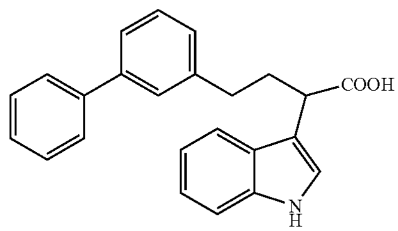 [SMILES: O=C(O)C(CCc1cccc(-c2ccccc2)c1)c1c[nH]c2ccccc12] |
| #23 | α-(2-Phenyl-1-ethyl)-3-indoleacetic acid | 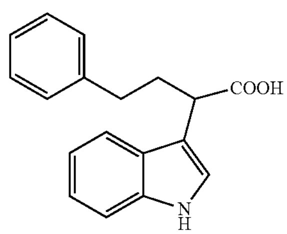 [SMILES: O=C(O)C(CCc1ccccc1)c1c[nH]c2ccccc12] |
| #24 | α-(2-Cyclopentyl-1-ethyl)-3-indoleacetic acid | 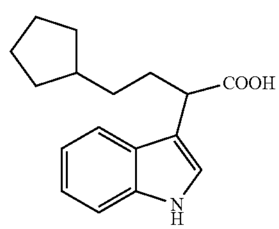 [SMILES: O=C(O)C(CCC1CCCC1)c1c[nH]c2ccccc12] |
| #25 | α-Cyclopentylmethyl-3-indoleacetic acid | 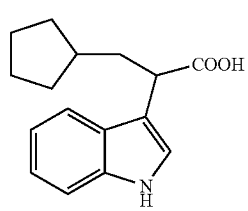 [SMILES: O=C(O)C(CC1CCCC1)c1c[nH]c2ccccc12] |

TABLE 1-continued
Exemplary compounds which can be produced
| Compound Number | Compound Name | Structure |
| --- | --- | --- |
| #26 | N-Methyl-3-indoleacetic acid | 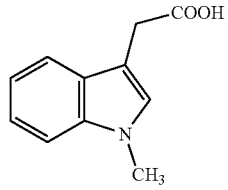 |
| #27 | N-Ethyl-3-indoleacetic acid | 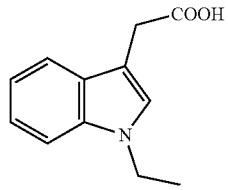 |
| #28 | N-Propyl-3-indoleacetic acid | 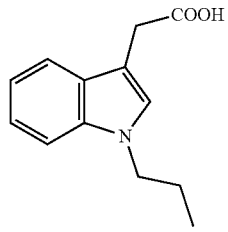 [SMILES: CCCn1cc(CC(=O)O)c2ccccc21] |
| #29 | N-Butyl-3-indoleacetic acid | 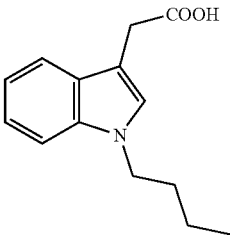 [SMILES: CCCCn1cc(CC(=O)O)c2ccccc21] |
| #30 | N-Hexyl-3-indoleacetic acid | 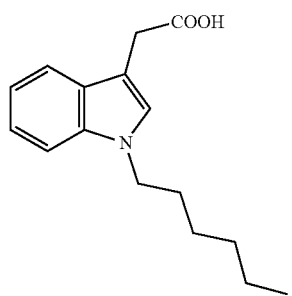 [SMILES: CCCCCCn1cc(CC(=O)O)c2ccccc21] |
| #31 | N-Heptyl-3-indoleacetic acid | 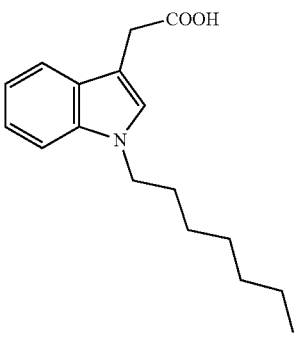 [SMILES: CCCCCCCn1cc(CC(=O)O)c2ccccc21] |

TABLE 1-continued

Exemplary compounds which can be produced

| Compound Number | Compound Name | Structure |
|---|---|---|
| #33 | α-(7-Butoxy-1-naphthalenyl)-acetic acid | 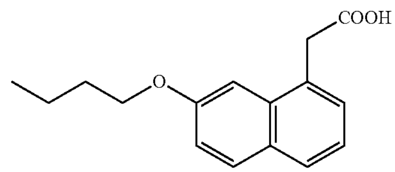 [SMILES: CCCCOc1ccc2cccc(CC(=O)O)c2c1] |
| #34 | α-(7-Pentoxy-1-naphthalenyl)-acetic acid | 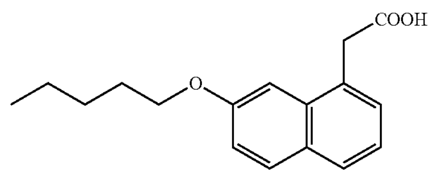 [SMILES: CCCCCOc1ccc2cccc(CC(=O)O)c2c1] |
| #35 | 5-(3,5-Dimethoxybenzyloxy)-3-indoleacetic acid | 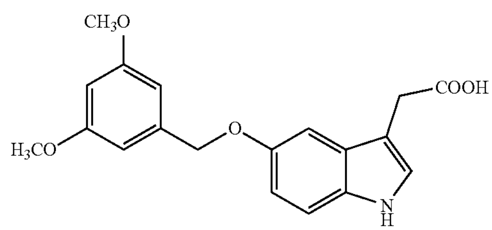 |
| #36 | 5-Methoxy-3-indoleacetic acid | 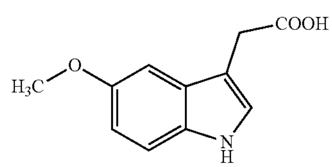 |
| #37 | 5-Ethoxy-3-indoleacetic acid | 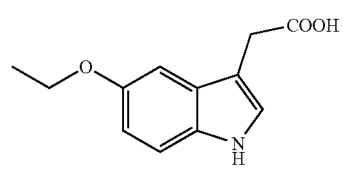 [SMILES: CCOc1ccc2[nH]cc(CC(=O)O)c2c1] |
| #38 | 5-(1-Propoxy)-3-indoleacetic acid | 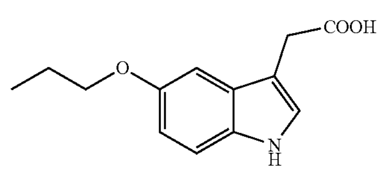 [SMILES: CCCOc1ccc2[nH]cc(CC(=O)O)c2c1] |
| #39 | 5-(1-Butoxy)-3-indoleacetic acid | 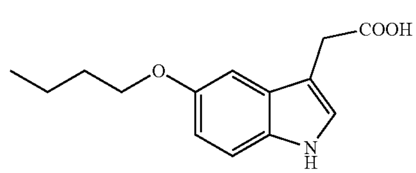 [SMILES: CCCCOc1ccc2[nH]cc(CC(=O)O)c2c1] |

EXAMPLES

The present invention will be specifically described with reference to Reference Examples, Examples and Test Examples, but it is not intended to be limited thereto. It is to be understood that the compound names given in Reference Examples and Examples do not necessarily conform to the IUPAC Nomenclature.

For simplicity of the description in the specification, the following abbreviations are also sometimes used in the Tables in Reference Examples, Examples and Test Examples. As an abbreviation, DMSO-d6 refers to deuterodimethyl sulfoxide. For symbols used for NMR, s refers to a singlet, d refers to a doublet, dd refers to a double doublet, m refers to a multiplet, brs refers to a broad singlet, and J refers to a coupling constant.

Reference Example 1

Production of trans-4-(2,4-difluorophenyl)-4-oxo-2-butenoic acid

Aluminum chloride (7.71 g) was added to an ice-cooled solution of maleic anhydride (2.58 g) in dichloromethane (26 mL), and 1,3-difluorobenzene (3.00 g) was added dropwise thereto. After completion of the dropwise addition, the mixture was stirred at room temperature for two hours. The reaction mixture was poured into an ice-cooled 1 mol/L solution of hydrochloric acid (150 mL) and extracted with chloroform containing 10% methanol. The organic layer was dried over anhydrous sodium sulfate and then concentrated under reduced pressure to give the title compound (5.16 g).

$^1$H-NMR (400 MHz, DMSO-$d_6$) δ: 13.23 (1H, brs), 7.96-7.90 (1H, m), 7.57 (1H, dd, J=15.6, 3.4 Hz), 7.50-7.44 (1H, m), 7.30-7.25 (1H, m), 6.62 (1H, d, J=15.6 Hz).

Reference Example 2

Production of trans-4-(4-fluorophenyl)-4-oxo-2-butenoic acid

Maleic anhydride (3.1 g) and aluminum chloride (9.1 g) were added to an ice-cooled solution of fluorobenzene (3.0 g) in dichloromethane (30 mL), and then stirred at room temperature for four hours. The reaction mixture was poured into ice water, and concentrated hydrochloric acid was then added thereto to adjust the pH of the solution to 1. The solution was subjected to separation and extraction by adding chloroform and water thereto, and the resulting organic layer was washed successively with 1 mol/L hydrochloric acid and a saturated sodium chloride solution, followed by drying over anhydrous sodium sulfate and concentrating under reduced pressure to give the title compound (4.8 g).

$^1$H-NMR (300 MHz, DMSO-$d_6$) δ: 13.19 (1H, brs), 8.13 (2H, dd, J=8.8, 5.5 Hz), 7.88 (1H, d, J=15.6 Hz), 7.42-7.37 (2H, m), 6.68 (1H, d, J=15.4 Hz).

Example 1

Production of 4-(2,4-difluorophenyl)-2-(1H-indol-3-yl)-4-oxobutanoic acid (#5)

Indole (0.703 g) was added to a solution of the compound of Reference Example 1 (1.16 g) in toluene (12 mL) and then was heated under reflux for three hours. After cooling to room temperature, the precipitated solid was collected by filtration and washed with toluene and hexane to give a crude product. The crude product was recrystallized from acetone/water. The resulting solid was collected by filtration, washed with acetone and water, and then dried to give the title compound (1.39 g).

$^1$H-NMR (400 MHz, DMSO-$d_6$) δ: 12.23 (1H, brs), 11.02 (1H, brs), 8.01-7.95 (1H, m), 7.63 (1H, d, J=7.8 Hz), 7.46-7.40 (1H, m), 7.36 (1H, d, J=8.3 Hz), 7.27-7.22 (2H, m), 7.11-7.07 (1H, m), 7.02-6.98 (1H, m), 4.33 (1H, dd, J=10.6, 4.1 Hz), 3.94-3.84 (1H, m), 3.32-3.26 (1H, m).

Example 2

Production of 4-(4-fluorophenyl)-2-(1H-indol-3-yl)-4-oxobutanoic acid (#4)

Indole (317 mg) was added to an 80° C. solution of the compound of Reference Example 2 (500 mg) in toluene (10 mL) and then heated under reflux for one hour. The reaction mixture was cooled to room temperature, the precipitated solid was then collected by filtration and washed with toluene and hexane to give a crude product. The crude product was recrystallized from acetone/water. The resulting solid was collected by filtration, washed with acetone, and then dried to give the title compound (250 mg).

$^1$H-NMR (300 MHz, DMSO-$d_6$) δ: 12.17 (1H, brs), 11.02 (1H, brs), 8.15-8.11 (2H, m), 7.67 (1H, d, J=7.7 Hz), 7.39-7.33 (4H, m), 7.11-7.06 (1H, m), 7.03-6.98 (1H, m), 4.33 (1H, dd, J=10.7, 3.9 Hz), 4.03 (1H, dd, J=18.1, 10.7 Hz), 3.36-3.29 (1H, m).

Example 3

Production of 4-(4-cholorophenyl)-2-(1H-indol-3-yl)-4-oxobutanoic acid (#2)

The title compound was synthesized according to the method described in Journal of the Chemical Society of Pakistan, 1985, 263-272.

Test Example 1: Inhibitory Effect on Cell Death of ALS Patient-Derived Fibroblasts Induced by Oxidative Stress ALS patient-derived fibroblasts can be used to confirm the inhibitory effect of the compound of the present invention on cell death induced by treating the ALS patient-derived fibroblasts with the glutathione synthesis inhibitor, L-buthionine(S, R)sulfoximine (BSO).

(Method 1)

$6.4 \times 10^3$ Cells per well of ALS patient-derived fibroblasts were seeded in a 96-well cell culture plate using a DMEM medium containing 1% FBS. One day after cell seeding, BSO was mixed in the culture medium so that the concentration thereof was 100 μmol/L. After culturing in the presence of BSO for one day, the compound of Example 1 was mixed in the culture medium so that the concentration thereof is 1, 3, 10 or 30 μmol/L. After culturing in the presence of the compound for another two days, the number of living cells in each well was counted by using Cell Counting Kit-8 (manufactured by Dojindo Laboratories) to calculate cell viability. Here, wells to which both BSO and the compound were not added but distilled water and DMSO that were solvents for BSO and the compound, respectively were added were used as a control of the oxidative stress loading; wells to which both BSO and the compound were added were used as a control for the effect of the test compound.
(Result 1)

The compound of Example 1 statistically significantly inhibited cell death induced by 100 μmol/L of BSO at concentrations of 10 and 30 μmol/L (FIG. 1). This result suggested that the compound of the present invention may ameliorate the pathological conditions of ALS by inhibiting cell damage induced by oxidative stress in ALS patients.
(Method 2)

$3.0 \times 10^3$ Cells per well of ALS patient-derived fibroblasts were seeded in a 96-well cell culture plate using a DMEM (low glucose) medium containing 1% FBS. One day after cell seeding, BSO was mixed in the culture medium so that the concentration thereof is 500 μmol/L. After culturing in the presence of BSO for one day, the compound of Example 1 was mixed in the culture medium so that the concentration thereof is 0.1, 0.3, 1, 3 or 10 μmol/L. After culturing in the presence of the compound for another three days, the number of living cells in each well was counted by using Cell Counting Kit-8 (manufactured by Dojindo Laboratories) to calculate cell viability. In addition, the degree of cell damage was measured by using LDH Cytotoxicity Detection Kit (manufactured by Takara Bio Inc.). Here, wells to which both BSO and the compound were not added but distilled water and DMSO that were solvents for BSO and the compound, respectively were added were used as a control of the oxidative stress loading; wells to which both BSO and the compound were added were used as a control for the effect of the test compound.
(Result 2)

The compound of Example 1 statistically significantly prevented the low cell viability and cytotoxicity induced by 500 μmol/L of BSO at concentrations of 0.1, 0.3, 1, 3 and 10 μmol/L (FIG. 2). This result suggested that the compound of the present invention may ameliorate the pathological conditions of ALS by inhibiting cell damage induced by oxidative stress in ALS patients.

Test Example 2: Inhibitory Effect on Cell Death of Fibroblasts Derived from Patients with Amyotrophic Diseases Other than ALS Induced by Oxidative Stress The inhibitory effect of the compound of the present invention on cell death of fibroblasts derived from patients with various amyotrophic diseases induced by oxidative stress can be confirmed by using fibroblasts derived from patients with amyotrophic diseases other than ALS according to the same as or similar to the above-mentioned methods.

Test Example 3: Amelioration Effect on Pathological Conditions-Related Phenotype Confirmed by Using Induced Pluripotent Stem Cells (iPS Cells) Derived from Patients with Amyotrophic Diseases The effect of the compounds of the present invention on the phenotype of cells considered to be related to the pathological conditions of amyotrophic diseases can be confirmed by using induced pluripotent stem cells (iPS cells) derived from patients with amyotrophic diseases according to the test method described in the reference literature (for example, Science Translational Medicine 4: 145ra104, 2012) or the similar method.

Test Example 4: Inhibitory Effect on Symptom Progression of ALS Animal Models (Wobbler Mice)

Wobbler mice are animals that exhibit progressive muscular atrophy and muscle flexion contraction of the forelimbs, resulting in gait disorder and movement disorder, and are used as animal models reflecting the pathological conditions of ALS. Therefore, the amelioration effect of the compound of the present invention on ALS-like symptoms exhibited by the animal models can be confirmed by using wobbler mice according to the method described in the reference literature (for example, Brain Research 1019: 226-236, 2004) or the similar method. Accordingly, in order to investigate the effect of the compound of the present invention on ALS-like symptoms exhibited by the wobbler mice, evaluation was performed by using rotarod walking time as an indicator.
(Method)

To 4-week-old wobbler mice, the compound of Example 1 (150 mg/kg) or a solvent, a 0.5% aqueous solution of methyl cellulose as a control was orally administered at a rate of 10 mL/kg once a day. Sixteen days after administration start date, the animals were placed on a mouse rotarod (manufactured by Muromachi Kikai Co., Ltd.) set at a rotation speed of 10 rpm and the time to fall was measured (rotarod test). The rotarod walking time was measured three times, and the upper limit of one measurement time was 300 seconds. If the animal did not fall even after exceeding 300 seconds, it was recorded that the rotarod walking time exceeded 300 seconds.
(Result)

In the rotarod test performed 16 days after administration start date, the occurrence ratio (%) of animals whose walking time exceeded 300 seconds was 86% in the group to which the compound of Example 1 was administered (n=14), in contrast to 43% in the control group (n=14) (FIG. 3), showing that the occurrence ratio of animals whose walking time exceeded 300 seconds was significantly increased in the group to which the compound of Example 1 was administered (P=0.018, chi-square test). These results suggested that the compound of the present invention can ameliorate the pathological conditions of ALS patients.

Test Example 5: Muscular Strength Improvement Effect on Animal Models with Disuse Muscle Atrophy The amelioration effect of the compound of the present invention on disuse muscle atrophy-like symptoms exhibited by the animal models can be confirmed by using the animal models with myogenic amyotrophic disease such as disuse muscle atrophy induced by plaster fixation and the test method described in the reference literature (such as Journal of Applied Physiology 106: 2049-2059, 2009, Journal of Physiological Sciences 61: 537-546, 2011) or the similar method.

More specifically, one or both of the hindlimbs of the mouse are fixed in a stretched or flexion state with plaster, the mouse is bred in that state for about one to two months, the plasters are removed, and the walking function of the mouse is measured by using a treadmill device. At that time, the effect of the compound of the present invention on disuse muscle atrophy can be confirmed by administering the compound after the plaster fixation.

In the above test, conditions such as a plaster treatment method, an administration method or an evaluation indicator can be appropriately changed. For example, in addition to the behavioral pharmacology test, a biochemical characterization using the animal tissue after completion of the test can be performed. The test methods described in the reference literatures cited by the above reference literature, and the test methods in which the conditions of these test methods are appropriately changed can also be used.

Test Example 6: Muscular Strength Improvement Effect on Animal Models with Neurogenic Muscle Atrophy The amelioration effect of the compound of the present invention on neurogenic muscle atrophy-like symptoms exhibited by the animal models can be confirmed by using the animal models with neurogenic muscle atrophy induced by sciatic nerve neurectomy and the test method described in the reference literature (such as The FASEB Journal 26: 2986-2999, 2012) or the similar method.

Test Example 7: Muscular Strength Improvement Effect on Animal Models with Myogenic Muscle Atrophy The amelioration effect of the compound of the present invention on myogenic muscle atrophy-like symptoms exhibited by the animal models can be confirmed by using the animal models with myogenic muscle atrophy induced by administration of dexamethasone and the test method described in the reference literature (such as The Journal of Physiology 589: 4759-4776, 2011) or the similar method.

INDUSTRIAL APPLICABILITY

The compounds of the present invention are useful as a therapeutic agent for inhibiting muscle atrophy, more specifically as a therapeutic agent for neurogenic amyotrophic disorders such as amyotrophic lateral sclerosis (ALS) and myogenic amyotrophic disorders such as sarcopenia or disuse muscle atrophy.

The invention claimed is:

1. A method for treating amyotrophic lateral sclerosis, comprising administering, to a patient in need of treatment for amyotrophic lateral sclerosis, a compound selected from the following formulas

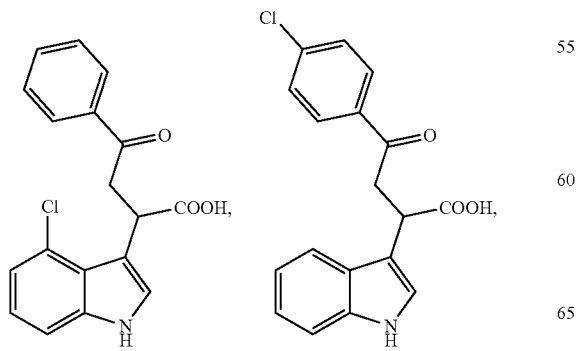

-continued

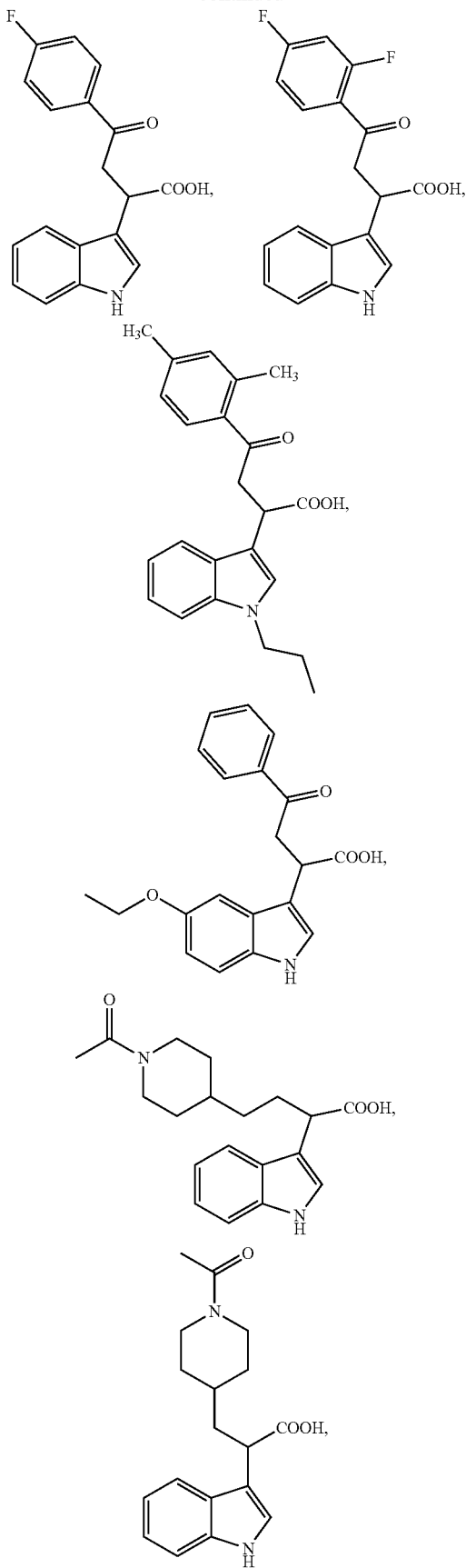

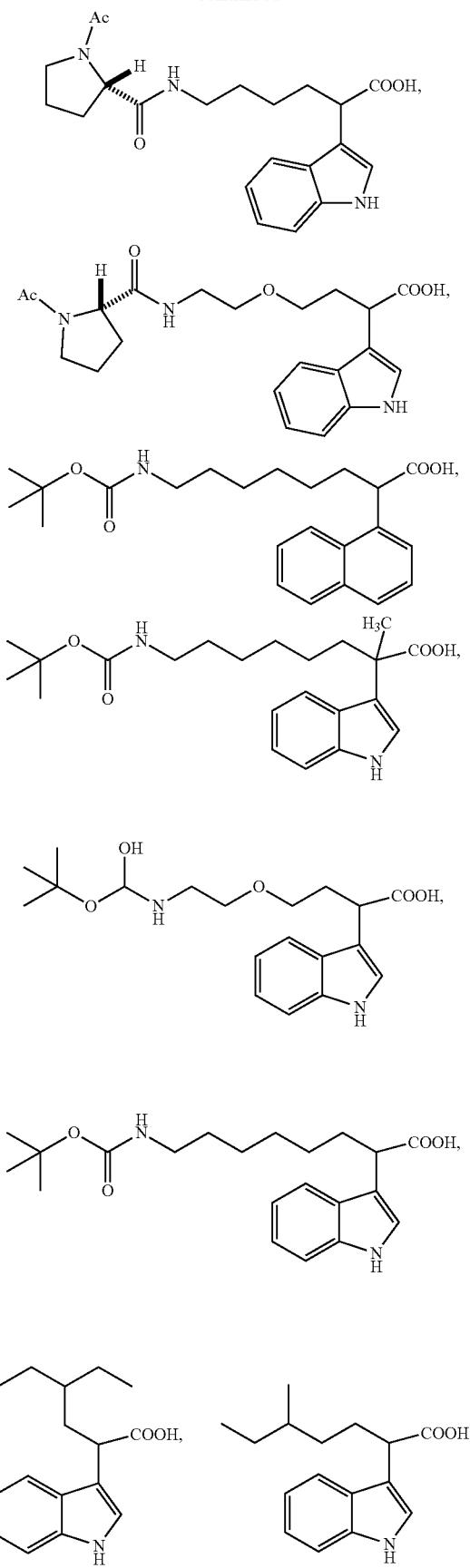
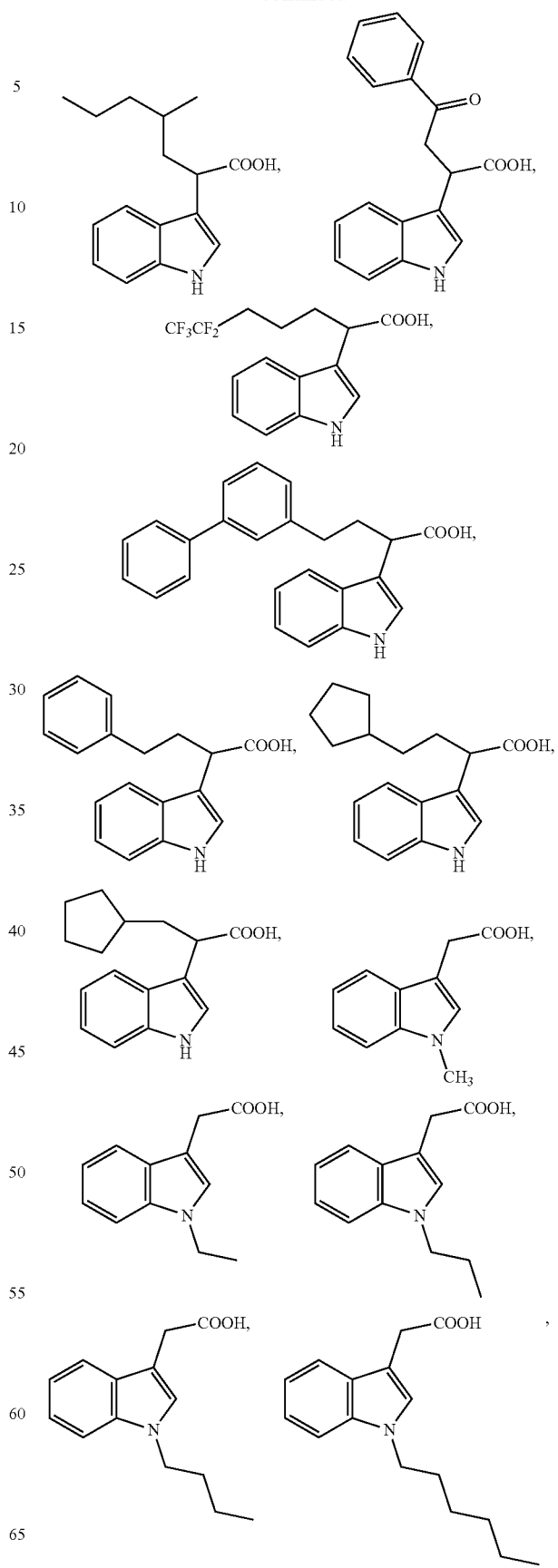

31
-continued
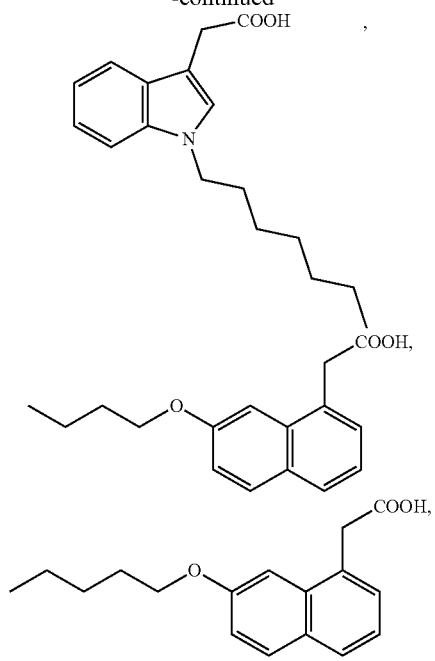
32
-continued
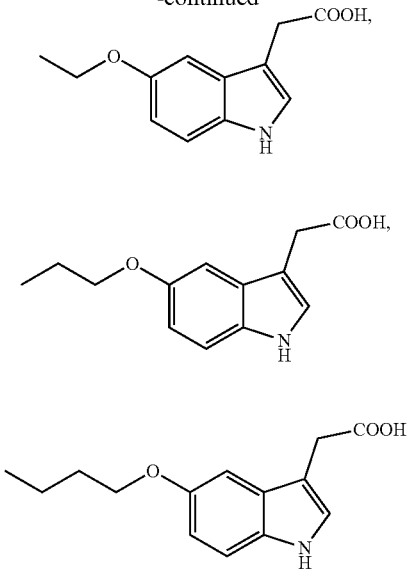
or a pharmaceutically acceptable salt thereof.
* * * * *